United States Patent [19]

Kawamura et al.

[11] Patent Number: 5,077,079

[45] Date of Patent: Dec. 31, 1991

[54] METHOD FOR FORMATION OF CALCIUM PHOSPHATE COMPOUND COATING ON SURFACE OF CERAMIC ARTICLE

[75] Inventors: Sukezo Kawamura, Inuyama; Yoshiyuki Yokogawa; Yukari Kawamoto, both of Nagoya; Motohiro Toriyama, Kasugai; Takahiro Suzuki, Nagoya, all of Japan

[73] Assignees: Agency of Industrial Science & Technology; Ministry of International Trade & Industry, both of Tokyo, Japan

[21] Appl. No.: 652,995

[22] Filed: Feb. 8, 1991

[30] Foreign Application Priority Data

Feb. 9, 1990 [JP]  Japan .................................. 2-30915

[51] Int. Cl.$^5$ .............................................. A01N 1/02
[52] U.S. Cl. ......................................... 427/2; 427/193; 427/203; 427/374.7; 427/376.6; 433/201.1; 433/212.1; 623/16
[58] Field of Search ............. 427/2, 202, 374.7, 376.6, 427/203, 193; 433/201.1, 212.1; 623/16

[56] References Cited

U.S. PATENT DOCUMENTS

| | | | |
|---|---|---|---|
| 4,308,064 | 12/1981 | Takami et al. | 623/16 |
| 4,617,279 | 10/1986 | Manabe et al. | 501/10 |
| 4,861,733 | 8/1989 | White | 623/16 |
| 4,983,182 | 1/1991 | Kijma et al. | 623/16 |
| 4,988,362 | 1/1991 | Toriyama et al. | 427/2 |

OTHER PUBLICATIONS

CRC Handbook of Chemistry and Physics, 63rd edition-p. B-88.

*Primary Examiner*—Shrive Beck
*Assistant Examiner*—Benjamin L. Utech
*Attorney, Agent, or Firm*—Oblon, Spivak, McClelland, Maier & Neustadt

[57] ABSTRACT

A dense coating of a calcium phosphate compound is formed on the surface of a bioadaptable ceramic substrate by applying to the ceramic calcium metaphosphate alone or a mixture of calcium metaphosphate with calcium pyrophosphate, heat-treating the applied layer thereby fusing the applied layer to the surface of the ceramic, then applying to the fused layer a slurry resulting from the mixture of calcium metaphosphate with tetracalcium phosphate, and subsequently heat-treating the applied layer of the slurry thereby inducing reaction of the slurry.

6 Claims, No Drawings

METHOD FOR FORMATION OF CALCIUM PHOSPHATE COMPOUND COATING ON SURFACE OF CERAMIC ARTICLE

BACKGROUND OF THE INVENTION

1. Field of the Invention

This invention relates to a method for the formation of a dense calcium phosphate compound coating on the surface of a ceramic article.

Calcium phosphate compounds possess high bioadaptability and are useful as materials for artificial bones, artificial roots of teeth, etc. for implantation in the human body. When these compounds are used as said materials, they are in the form of sintered articles. It is widely held, however, that sintered articles of calcium phosphate compounds are deficient in strength, toughness, resistance against abrasion, etc. Bioadaptable ceramic substances also include alumina, zirconia, etc. These ceramic substances, however, are inferior to the calcium phosphate compounds in bioadaptability. High-strength materials excelling in bioadaptability can be produced by forming coatings of calcium phosphate compounds on ceramic substrates of alumina, zirconia, etc.

2. Description of the Prior Art

Sintered articles of calcium phosphate compounds exhibit high bioadaptability but low mechanical strength. Efforts have been heretofore made to impart added strength to these sintered article as by incorporating such high-strength materials as zirconia into calcium phosphate compounds or by orienting crystals of calcium phosphate compounds in one direction as in crystallized glass.

Such a bioceramic is described in U.S. Pat. Application Ser. No. 07/319,757, now U.S. Pat. No. 4,988,362, for example. Some of the inventors of this patent are also inventors of the present application. The allowed claim is as follows.

"A method for fusion of a bioceramic to the surface of a bioceramic inert to vital tissues, comprising:

(A) coating the surface of said bioceramic inert to vital tissues with a bioceramic composition consisting essentially of a composition produced by mixing alumina and silica in a gravimetric ratio in the range of 1:2 to 1:4 thereby preparing a mixed powder and incorporating into said mixed powder a calcium phosphate compound in an amount in the range of 10 to 60% by weight, based on the amount of said mixed powder, thereby forming a coating layer on the surface of said bioceramic;

(B) heating said bioceramic inert to vital tissues now provided with said coating layer thereby converting said coating layer into a solid solution containing aluminum phosphate formed by the reaction of calcium phosphate compound with alumina; and (C) cooling the resultant of (B), thereby accelerating crystallization of the coating layer."

The invention defined by this claim still has the following problem.

The product of this fusion is inferior in bioadaptability and in bioaffinity to the material having calcium phosphate alone exposed on the surface because the coating layer of said product contains alumina, a substance deficient in bioadaptability, in a large amount at the surface thereof.

In this earlier invention, the calcium phosphate compounds rich in bioadaptability are represented by $\beta$-$Ca_3(PO_4)_3$, i.e. $\beta$-tricalcium phosphate (hereinafter referred to as "TCP"), and $Ca_{10}(OH)_2(PH_4)_6$, i.e. calcium hydroxy apatite (hereinafter referred to as "HAp"). TCP and HAp, however, do not easily unite directly with ceramic substrates. It is known that plasma frame spraying, CVD, etc. can be used for coating ceramic surfaces and are capable of producing union of high strength. However, production of thick coatings by these methods requires much time and the use of special expensive devices.

SUMMARY OF THE INVENTION

Conceived in the light of the state of prior art described above, this invention is directed to providing a novel method for the formation of a dense coating of calcium phosphate on a high-strength material.

This object is accomplished in accordance with this invention by a method, which comprises:

applying to the surface of a ceramic at least one member selected from the group consisting of calcium metaphosphate and a mixture of calcium metaphosphate with calcium pyrophosphate, heating the applied layer thereby fusing the applied layer to the surface of the ceramic, applying to the surface of the product of fusion a slurry of the mixture of calcium metaphosphate with tetracalcium phosphate, and subsequently heating the applied layer of the slurry thereby inducing reaction of the slurry.

Thus, this invention concerns a method for the formation of a dense coating of calcium phosphate on the surface of a ceramic.

DETAILED DESCRIPTION OF THE PREFERRED EMBODIMENTS

The method of this invention is initiated by the step of applying to the surface of a ceramic calcium metaphosphate, $Ca(PO_3)_2$, or a mixture of calcium metaphosphate with calcium pyrophosphate, $Ca_2P_2O_7$, and heat-treating the applied layer. Desirably, this heat treatment is performed at a temperature in the range of 900° to 1,100° C. where calcium metaphosphate alone is used or at a temperature in the range of 1,100° to 1,280° C. where the mixture of calcium metaphosphate with calcium pyrophosphate is used. By this heat treatment, the calcium metaphosphate or the mixture of calcium metaphosphate with calcium pyrophosphate is uniformly fused to the surface of the ceramic substrate.

The fusion is incomplete when the temperature of the heat treatment falls short of the specified range. The strength of the ceramic substrate is degraded when the temperature of the heat treatment exceeds the specified range.

When the mixture of calcium metaphosphate with calcium pyrophosphate is applied to the surface of a ceramic, the mixing ratio of calcium metaphosphate to calcium pyrophosphate is desired to be in the range of 3:7 to 7:3 by weight. The property of the mixture is substantially identical with the simple mass of calcium metaphosphate when the proportion of calcium metaphosphate exceeds the upper limit of the specified range.

The fusion of the applied layer of the mixture to the ceramic substrate fails unless the heat treatment is performed at a notably elevated temperature when the proportion of calcium pyrophosphate is unduly large.

Particularly desirably, the mixing ratio is in the range of 3:7 to 5:5 and the temperature of the heat treatment is in the range of 1,100° to 1,200° C.

The next step consists in applying a slurry resulting from the mixture of calcium metaphosphate with tetracalcium phosphate, $Ca_4(PO_4)_2O$, to the surface of the ceramic substrate already having calcium metaphosphate or the mixture of calcium metaphosphate with calcium pyrophosphate fused to the surface thereof and then heat-treating the applied layer of the slurry. Desirably, this heat treatment is performed at a temperature in the range of 1,200° to 1,350° C. The mixing ratio of calcium metaphosphate to tetracalcium phosphate is desired to be in the range of 1.2:1 to 2.0:1 as reduced to atomic ratio (Ca/P).

Although a coating of the calcium phosphate compound is obtained even when this mixing ratio deviates from the specific atomic ratio mentioned above, the following disadvantages arise:

(a) The produced coating contains apatite, $\beta$-calcium phosphate, and calcium pyrophosphate if the proportion of Ca is unduly large.

(b) The produced coating has a markedly high calcium pyrophosphate content if the proportion of P is unduly large.

From the practical point of view, therefore, the upper limit of the range of the mixing ratio is 1.75:1 and the lower limit thereof is 1.4:1.

The calcium compound formed on the surface of the ceramic substrate varies in type, depending on the mixing ratio of calcium metaphosphate to tetracalcium phosphate in the slurry to be applied to the product of fusion and the temperature of the heat treatment.

The HAp is obtained as the product of reaction on the surface of the ceramic substrate, for example, when the atomic ratio (Ca/P) is 1.67:1 and the temperature of the heat treatment is 1,300° C. The TCP is obtained instead when the atomic ratio (Ca/P) is 1.5:1 and the temperature of the heat treatment is 1,200° C.

Now, the process for the formation of TCP and HAp will be described below.

The calcium metaphosphate and the tetracalcium phosphate applied to the surface of the metaphosphate (formed by the heating of calcium metaphosphate or the mixture of calcium metaphosphate with calcium pyrophosphate) fused to the surface of the ceramic substrate interreact through the medium of the fused metaphosphate mentioned above. At this interreaction proceeds, it first produces calcium pyrophosphate and then gives rise to TCP and HAp (confirmed by X-ray diffraction spectrometry). The $\beta$-calcium pyrophosphate continues to exist predominantly up to 1,100° C. The formation of TCP and HAp commences when the temperature surpasses 1,150° C. When the TCP as a composition is heat-treated at a temperature exceeding 1,200° C. for a long time, it is transformed into the $\alpha$ phase with an accompanying conspicuous change in volume. Since this change in volume causes cracking, as between the coating and the ceramic substrate, the duration of this heat treatment is desired not to exceed one hour.

By the method of this invention, a high-strength material of outstanding bioadaptability can be produced which comprises a ceramic substrate, a coating layer of metaphosphate formed by the heat treatment of calcium metaphosphate or a mixture of calcium metaphosphate with calcium pyrophosphate and consequently fused to the surface of the ceramic substrate, and HAp or TCP united intimately and fast to the coating layer of metaphosphate.

Ceramic substances which can be effectively used in this invention include such bioadaptable substances as partially stabilized zirconia, alumina, etc.

Further, this invention allows a reduction of running cost in the manufacture of the coated product because the method has no need for any special expensive device.

Now, this invention will be described more specifically below with reference to working examples.

EXAMPLE 1

Calcium metaphosphate was applied to the surface of a substrate of partially stabilized zirconia (3 mol % yttria solid solved) and the applied layer of calcium metaphosphate was heat-treated at 1,000° C. for 30 minutes to fuse the applied layer to the surface of the substrate. A slurry obtained by mixing calcium metaphosphate with tetracalcium phosphate at an atomic ratio (Ca/P) of 1.5:1 was applied to the surface of the coating layer and the resultant layer was heat-treated at 1,200° C. for 40 minutes. The zirconia surface consequently obtained had the appearance of a dense coating. The X-ray diffraction spectrum of this coating revealed the occurrence of TCP and showed no diffraction peak of calcium metaphosphate or tetracalcium phosphate. In the coating thus formed, the intermediate layer or the fused layer of calcium metaphosphate had a thickness of 20 $\mu$m and the TCP layer a thickness of 100 $\mu$m.

EXAMPLE 2

A mixture obtained by mixing calcium metaphosphate with calcium pyrophosphate at an atomic ratio of 1:1 was applied to the surface of a substrate of partially stabilized zirconia (8 mol % yttria solid solved) and the applied layer of the mixture was heat-treated at 1,200° C. for 30 minutes and consequently fused to the surface of the substrate. A slurry obtained by mixing calcium metaphosphate with tetracalcium phosphate at an atomic ratio (Ca/P) of 1.67:1 was applied to the surface of the resultant coating layer and the applied layer of the slurry was heat-treated at 1,300° C. for 40 minutes. The zirconia surface consequently obtained had the appearance of a dense coating. The X-ray diffraction spectrum of this coating revealed the occurrence of HAp and showed no diffraction peak of calcium metaphosphate or tetracalcium phosphate. In the coating thus formed, the intermediate layer or the fused layer of calcium metaphosphate had a thickness of 20 $\mu$m and the layer of HAp had a thickness of 100 $\mu$m.

What is claimed is:

1. A method for forming on the surface of a ceramic substrate a dense coating composed of at least one member selected from the group consisting of $\beta$-tricalcium phosphate and calcium hydroxy apatite, which comprises the steps of:

applying to the surface of a ceramic substrate at least one compound selected from the group consisting of calcium metaphosphate and a mixture of calcium metaphosphate and calcium pyrophosphate;

heating the applied compound, thereby fusing the compound to the surface of said ceramic substrate;

applying to the fused compound a slurry consisting of a mixture of calcium metaphosphate and tetracalcium phosphate; and subsequently heating the applied slurry, thereby inducing reaction of the slurry to form a dense coating composed of at least one member selected from the group consisting of β-tricalcium phosphate and calcium hydroxy apatite.

2. A method according to claim 1, wherein said at least one compound applied to the surface of the ceramic substrate is calcium metaphosphate and is heated at a temperature in the range of 900° to 1,100° C.

3. A method according to claim 1, wherein said at least one compound applied to the surface of the ceramic substrate is a mixture of calcium metaphosphate and calcium pyrophosphate and is heated at a temperature in the range of 1,100° to 1,280° C.

4. A method according to claim 3, wherein the gravimetric mixing ratio of calcium metaphosphate to calcium pyrophosphate is in the range of 3:7 to 7:3.

5. A method according to claim 1, wherein the heat treatment given to the applied layer of the slurry consisting of calcium metaphosphate and tetracalcium phosphate is performed at a temperature in the range of 1,200° to 1,350° C.

6. A method according to claim 1, wherein the atomic ratio of calcium metaphosphate and tetracalcium phosphate in the applied slurry Ca/P, is in the range of 1.4:1 to 1.75:1.

* * * * *